United States Patent [19]

Nilles et al.

[11] 4,324,548
[45] Apr. 13, 1982

[54] LATCH MECHANISM FOR DENTAL HANDPIECE ASSEMBLY

[75] Inventors: John D. Nilles, Roselle; Stanley L. Stankiewicz, Chicago; David S. Zubriski, Mt. Prospect, all of Ill.

[73] Assignee: American Hospital Supply Corporation, Evanston, Ill.

[21] Appl. No.: 161,680

[22] Filed: Jun. 23, 1980

[51] Int. Cl.³ .................................................. A61C 1/08
[52] U.S. Cl. ..................................... 433/126; 403/325
[58] Field of Search ............... 433/126; 403/325, 328, 403/324, 24; 285/317, 7; 279/76, 89, 79, 80, 1 B

[56] References Cited

U.S. PATENT DOCUMENTS

| | | | |
|---|---|---|---|
| 796,527 | 8/1905 | Patchen | 433/126 |
| 3,604,735 | 9/1971 | Hoffmeister | 403/322 |
| 3,815,240 | 6/1974 | Loge | 433/126 |

Primary Examiner—R. Peshock
Attorney, Agent, or Firm—Tilton, Fallon, Lungmus

[57] ABSTRACT

A dental handpiece assembly equipped with an improved latch mechanism for detachably connecting a motor section to a straight or angular handpiece section. The latch includes a ring disposed between the two sections, the ring having an outer surface which is substantially flush with the casings of the respective sections when the parts are assembled and the ring is in its normal latching position. Unlatching is accomplished by displacing the entire ring in a transverse direction, by finger pressure applied at any point along a semi-circumferential area of the ring's outer surface, to shift an arcuate rib out of engagement with the neck portion of the other section of the assembly.

22 Claims, 8 Drawing Figures

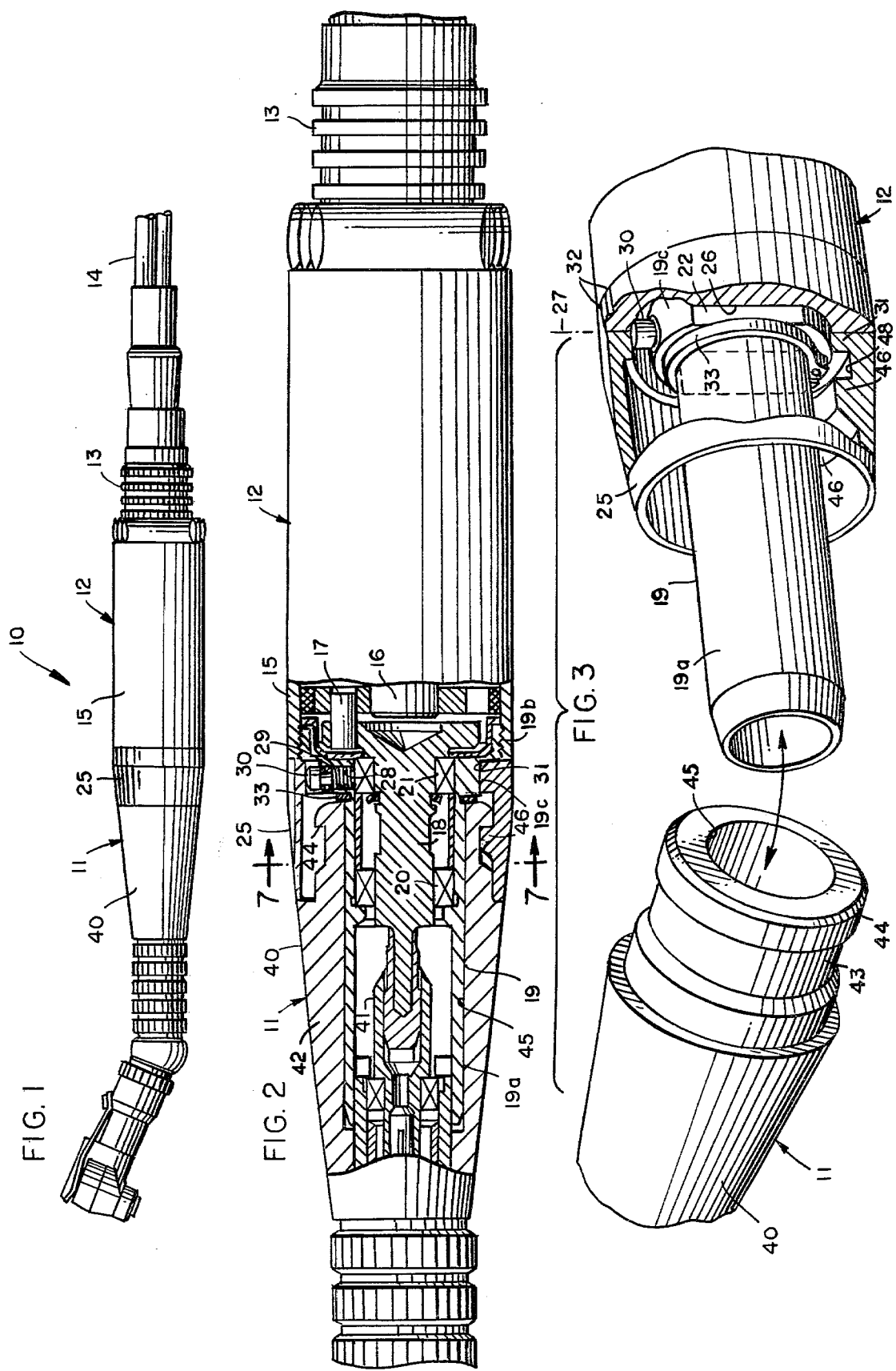

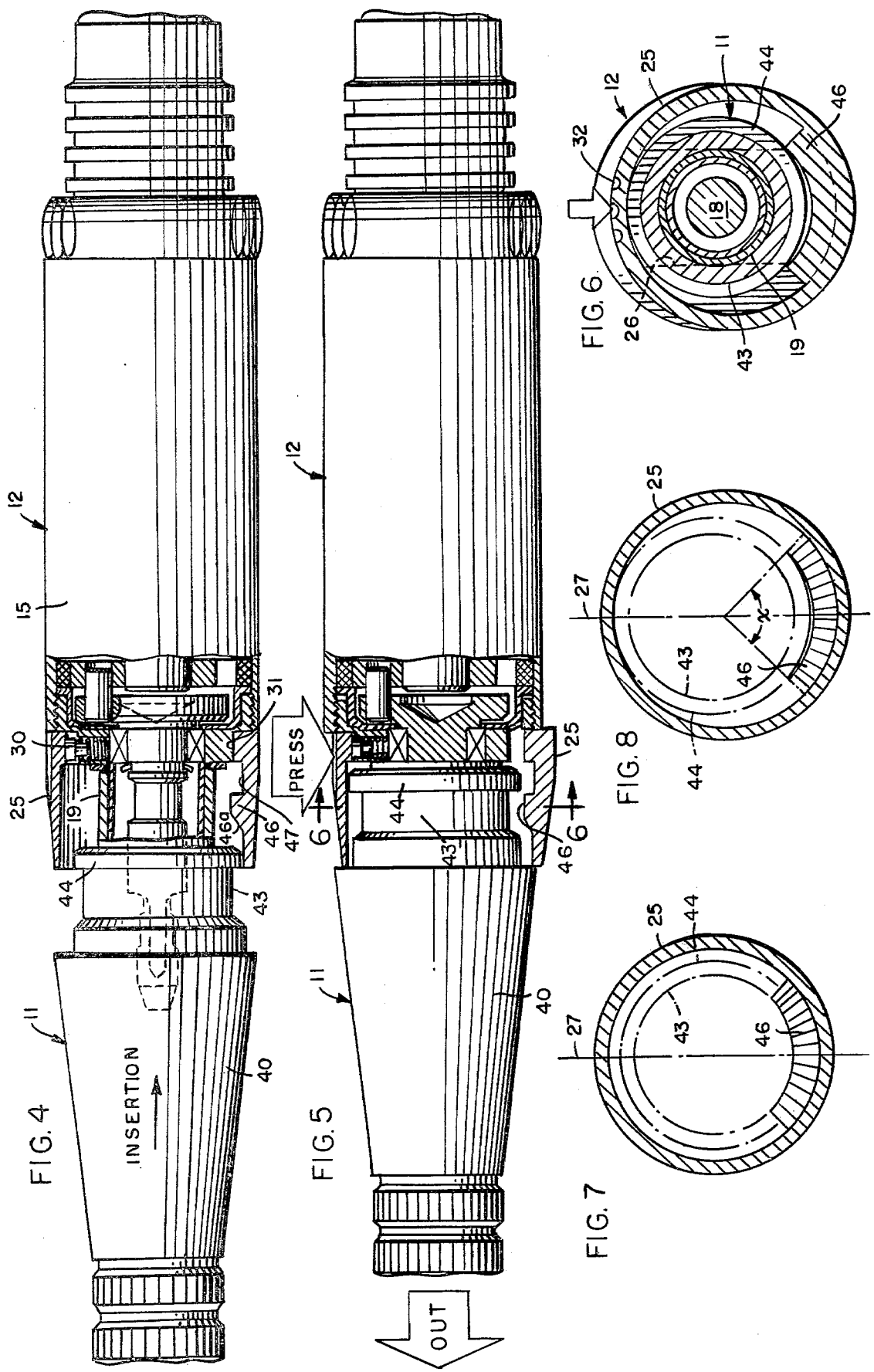

4,324,548

LATCH MECHANISM FOR DENTAL HANDPIECE ASSEMBLY

BACKGROUND AND SUMMARY

U.S. Pat. No. 3,432,194, including the prior art depicted and described in that patent, is illustrative of the type of coupling mechanism that has been used in the past to interconnect a handpiece motor section with any of a variety of straight or angular handpiece attachment sections. The coupling takes the form of a slip joint with one of the sections, usually the motor section, having a cylindrical sleeve adapted to be received within a socket in the other (handpiece) section. An external or internal latch connects the two parts to prevent axial separation without preventing relative rotation. In general, such a latch mechanism has a substantial axial length and the push button or other means for actuating the latch projects laterally from the outer surface of the handpiece section in which it is provided. The lateral projection of the button from the assembly is undesirable because it tends to increase the risk of inadvertent release of the latch. Although that risk may be reduced somewhat by decreasing the size of the button and the extent of lateral projection thereof, such modifications increase the difficulty of intentionally manipulating the latch when disengagement of the parts is desired. See also U.S. Pat. No. 3,604,735.

Other types of latching mechanisms have been devised, some of which include rings that do not project significantly beyond the outer surface of the handpiece and motor sections, the latches being actuated either by rotation of the rings or by axial displacement of such rings. (For an example of the latter, see U.S. Pat. No. 3,665,606). Where the mode of operation requires axial displacement of a latch ring, an undesirable axial spacing is commonly provided to accommodate such movement. In the case of a rotatable latch ring, a user may find manipulation difficult since two hands may be required to turn the ring relative to the motor section and then one of the hands must be shifted to urge the two sections axially apart.

The present invention lies in providing an assembly equipped with a latch mechanism which overcomes such defects and disadvantages of prior constructions. The latch mechanism, although capable of being released by the application of force over a substantial semi-circumferential area, is not likely to be inadvertently actuated because when the sections are latched together the latching element, in the form of a latching ring, has its outer surface flush with the outer surfaces of the handpiece and motor sections.

The latch mechanism of this invention is highly reliable in operation, providing relatively large latching surfaces which are less likely to wear, and become insecure by reason of such wear, than prior latch mechanisms. In addition, the latch ring or tube allows the flow of air therethrough for the purpose of cooling the bearings of the motor section and the handpiece attachment section.

Briefly, the assembly takes the form of a motor section and a handpiece section, each having a power-transmitting shaft or spindle axially disposed therein. When assembled, the sections are arranged in longitudinal alignment with the respective power-transmitting shafts thereof in operative engagement with each other. The latch ring or tube is carried by one of the sections, preferably the motor section, and is disposed between the two sections with its outer surface normally in flush relation with the outer surfaces of the adjoining sections. The ring is mounted to permit limited transverse movement thereof into an unlatching position, in which position an arcuate rib or projection formed within the ring is disengaged from a neck portion of the handpiece section to permit axial separation of the parts. In the absence of the application of force displacing the ring laterally into its unlatching position, a spring maintains the ring in latching condition. The ring has substantial axial length and, since it may be moved into its unlatching position by finger contact over an arc of its surface of approximately 180°, it provides a large contact area for finger engagement and operation. However, because its outer surface is normally flush with the casings of the handpiece and motor sections, the possibilities of snagging or otherwise interfering with manipulation of the handpiece, or of inadvertent release of the latch, are virtually eliminated.

Other features, objects, and advantages of the invention will become apparent from the specification and drawings.

DRAWINGS

FIG. 1 is a side elevational view of a handpiece-motor assembly equipped with the latching mechanism of this invention.

FIG. 2 is an enlarged elevational view taken partly in section and illustrating the coupling between the handpiece and motor sections.

FIG. 3 is an enlarged fragmentary perspective view showing the handpiece and motor sections in separated condition with the latching ring partially cut away to reveal internal structural features of the latch mechanism.

FIG. 4 is a side elevational view, taken partly in section, illustrating the relationship of the motor and handpiece sections as they are being advanced into latched condition.

FIG. 5 is a longitudinal view similar to FIG. 4 but showing the handpiece and motor sections after they have been coupled, and with the latch ring displaced laterally to unlatch the sections for disengagement and separation.

FIG. 6 is a cross sectional view taken along line 6—6 of FIG. 5.

FIG. 7 is a cross sectional view of only the latch ring, taken along line 7—7 of FIG. 2, illustrating the arcuate shoulder or lug responsible for latching the handpiece and motor sections together.

FIG. 8 is a sectional view similar to FIG. 7 but showing with the aid of phantom lines the relationship of parts when the ring is in its unlatching position.

DETAILED DESCRIPTION

In the drawings, the numeral 10 generally designates an assembly composed of handpiece section 11 and motor section 12. The motor section is generally cylindrical and is shown connected by means of coupling 13 to hoses 14 for supplying air and water to the handpiece and, at least in some cases, for carrying exhaust air away from the handpiece. Coupling 13 and hose assembly 14 are conventional and are shown simply for illustrative purposes. The hose assembly may be detached from the assembly 10 by unscrewing the coupling 13 from the threaded stem (not shown) of the motor section.

The motor section has a tubular cylindrical casing 15 which houses an airmotor 16, only the drive shaft of which is illustrated in FIG. 2. The airmotor may be of any conventional type designed to be operated by pressurized air supplied by hose assembly 14. Motor output shaft 16 is engaged by planet gears rotating on pins 17 carried by a spindle or power transmission shaft 18 which extends axially from the distal end of motor casing 15. A pilot sleeve 19 has an elongated tubular portion 19a which extends distally beyond spindle 18, the pilot sleeve being enlarged and threaded at its proximal end 19b for attachment to the internally threaded distal end of casing 15 (FIG. 2). Within the tubular portion of the pilot sleeve are a pair of bearing assemblies 20 and 21 for rotatably supporting spindle 18.

The pilot sleeve 19 also includes an intermediate portion 19c which has an outside dimension larger than elongated tubular portion 19a but smaller than the enlarged threaded proximal portion 19b. As shown in FIG. 2, portion 19c is located just beyond the distal end of motor casing 15. It will also be observed from FIG. 3 that the outer surface of intermediate portion 19c is not cylindrical but instead has a pair of flat parallel side surfaces 22 for guiding transverse movement of the latch ring described hereinafter.

In the embodiment illustrated, the latch ring 25 appears as a forward or distal extension of motor casing 15. Internally, the latching ring or tube has a diameter substantially greater than the elongated distal portion 19a of the pilot sleeve but, adjacent its proximal end, the ring is provided with a pair of shoulders 26 defining spaced parallel surfaces which slidably engage the lateral surfaces 22 of the pilot sleeve's intermediate portion 19c (FIG. 3). The latching ring is therefore capable of limited bi-directional transverse movement along a path of movement represented in FIG. 3 by line 27, such line extending diametrically through the motor section 12 and being parallel with guide surfaces 22 and shoulder surfaces 26.

The intermediate portion 19c of the pilot sleeve 19 is provided with a radially inwardly extending recess or bore 28 which contains compression spring 29 (FIG. 2). The spring exerts an outward force on contact member or pin 30 which in turn bears against the inside surface of the latching ring 25 to urge the ring into the latching position depicted in FIGS. 2 and 3. In that position, the outer surface of the latching ring or tube is substantially flush with the outer surface of motor casing 15. The arcuate inside surface 31 of the latch ring on the opposite side of that ring from contact member 30 bears against the intermediate portion 19c of the pilot sleeve when the ring is in its latching position, thereby serving as a stop to maintain the ring in axial alignment with the motor casing 15.

Contact member 30, spring 29, and recess 28 all extend along transverse line 27 which defines the path of transverse movement of the latch ring between its latching and unlatching positions. Lateral finger pressure on the ring 25 that serves to cause retraction of member 30 and compression of spring 29 will result in movement of the ring into the unlatching position depicted in FIGS. 5 and 6. It is not necessary that the point of finger contact be in direct alignment with contact member 30; although contact at that point is preferred for ease of operation, it is possible to displace the ring into its unlatching position by finger contact over an area extending approximately 90° either way from the optimum point. Since the ring is of substantial length (its total length being approximately 30 to 150% of its maximum outside diameter, and preferably over 50%, the ratio depicted in the drawings being approximately 66%), it is believed apparent that an extremely large area for actuation by finger contact, totaling approximately one half of the outside surface area of the ring, is provided. To help the user in directing finger pressure to that area of actuation, the outside surface of the sleeve (or, if desired, the outside surface of the motor casing 15) may be provided with one or more index grooves 32 aligned with contact member 30. Any other suitable indicia may be provided; however, longitudinal grooves 32 are believed particularly effective because they help the user locate the target area by touch as well as by sight and, in addition, reduce the possibility that in applying pressure the user's finger will not slip laterally over the curved surface of the ring.

Referring to FIGS. 2 and 3, the latch ring 25 is shown to be held in operative position as part of the motor section 12 by a spring retention clip or ring 33 received in a groove at the proximal end of the reduced tubular portion 19a of pilot sleeve 19. It is to be understood, of course, that any other suitable retaining means may be used for preventing axial movement of the latch ring with regard to the remaining parts of the motor section 12 without preventing limited transverse movement of the ring between its latching and unlatching positions.

Handpiece section 11 is shown in FIG. 1 as a contra angle attachment; however, it is to be understood that section 11 may constitute a straight attachment rather than a contra angle unit, and that such attachment may be shorter, longer, or have a configuration considerably different than the one depicted. Such variations are all well known in the art and need not be detailed here. What is critical is that the handpiece section have a casing 40 adapted to be coupled to the motor section by means of latch ring 25, and that internally the handpiece section have a spindle or shaft 41 adapted to engage the spindle 18 of the motor section for transmitting power to the handpiece bur tube (not shown) when the parts are assembled for use. In the illustration given, handpiece casing 40 has a frusto-conical portion 42 which provides a surface flush with that of latch ring 25 when the components of the handpiece are assembled (FIGS. 1 and 2). For that purpose, the outer surface of the latch ring is shown to have a cylindrical rear portion which matches the outside dimensions of the motor casing 15 and a frusto-conical front portion which matches the outside surface of handpiece casing portion 42.

The handpiece casing 40 is provided at its proximal end with a reduced neck portion 43, the neck terminating in an enlarged annular lip or flange 44. A bore or socket 45 extends into the handpiece casing 40 from the proximal end thereof (FIG. 3) and is dimensioned for slidably receiving the elongated stem portion 19a of the pilot 19 of motor section 12.

The inside surface of latch ring 25 is provided with an arcuate projection or rib 46 which is positioned to engage the flange 44 of the handpiece casing 40 when the parts are assembled as shown in FIG. 2. The arcuate rib is located along the inside of the ring 25 in an area opposite from the retractable contact member 30 and directly in front of arcuate surface 31. When the neck 43 of the handpiece casing 40 is fitted upon pilot sleeve 19 of the motor section and is then directed into the open mouth of the latch ring 25, in the manner depicted in FIG. 4, flange 44 will be advanced into contact with the sloping distal surface 46a of the rib 46, thereby automatically camming the latch ring 25 out of axial alignment with motor casing 15 until flange 44 clears the rib and is received in the space 47 between rib 46 and surface 31. The latch ring 25 will then be returned by spring 29 and contact member 30 into its original coaxial latching position shown in FIG. 2. Since flange 44 is annular, such latching will occur regardless of the particular relative rotation of the two sections 11 and 12 about their common axis. For the same reason, following a latching operation, the two sections 11 and 12 may be rotated with respect to each other without disengaging the latch.

Unlatching of the parts occurs in the manner already indicated. The user simply presses the latch ring 25 in a semi-circumferential area overlying spring 29 and contact member 30 to cause lateral displacement of the ring into the unlatching position depicted in FIGS. 5 and 6. The flanged neck portion 43 of the handpiece casing will then be free to be withdrawn axially from latch ring 25 and pilot sleeve 19.

The latching and unlatching relationships may be more readily apparent from the simplified cross sectional views of FIGS. 7 and 8 in which only the latch ring 25 is illustrated in solid lines. Phantom lines 44 represents the outer limits of the annular flange, whereas line 43 delineates the outer surface of the neck directly ahead of (i.e., distal to) that flange. When the parts are latched together, the arcuate rib or projection 46 blocks axial retraction of the flanged handpiece casing (FIG. 7), whereas when the latch ring is displaced along transverse line 27 in the direction of arrow 48, the arcuate rib is shifted laterally a distance sufficient to permit uncoupling of the parts. It is to be noted that the rib or projection has a substantial angular extent to insure secure interlocking of the parts and to eliminate, or at least greatly reduce, any possibility that wear of the latching elements (rib 46 and flange 44) might reduce the security of the latch to the point that accidental disengagement might take place. Specifically, angle x shown in FIG. 8 should be more than 20° and preferably in the range of 60° to 100°, the particular angle shown being approximately 90°.

While in the foregoing an embodiment of the invention has been shown in considerable detail for purposes of illustration, it will be understood by those skilled in the art that many of these details may be varied without departing from the spirit and scope of the invention.

We claim:

1. A dental handpiece assembly comprising a motor section and a handpiece section having a motor casing and a handpiece casing, respectively; each of said sections having a power-transmitting shaft axially disposed therein; said sections normally being disposed in longitudinal alignment with the respective power-transmitting shafts thereof in operative engagement with each other; and latching means releasably connecting said sections in operative relationship; wherein the improvement comprises said latching means including a tubular latching ring provided by said motor section adjacent said handpiece section; said latching ring having a circumferentially-exposed annular outer surface continuing axially beyond the outer surface of said motor section; means mounting said ring for transverse movement between a latching position wherein said ring is coaxial with said motor section and has its annular outer surface substantially aligned with the outer surface of said motor section and an unlatching position wherein said ring is displaced laterally relative to said motor section; a spring urging said ring into said latching position; said handpiece casing having a tubular neck provided with an annular flange disposed within said ring when said sections are latched together; and an arcuate projection provided within said ring and engaging said neck and flange to prevent axial separation of said sections when said ring is in its latching position; said projection being shifted laterally away from said neck and flange when said ring is urged into its unlatching position for disconnection of said section.

2. The assembly of claim 1 in which said spring exerts an outward force upon said ring extending along a diametric line of ring movement; said arcuate projection extending through said diametric line of movement.

3. The assembly of claim 2 in which said diametric line of ring movement is fixed relative to said motor section.

4. The assembly of claims 2 or 3 in which said spring is a helical compression spring disposed along said diametric line of movement on one side of said motor section and within said ring, and said arcuate projection is disposed along said diametric line of movement on the opposite side of said motor section within said ring.

5. The assembly of claim 4 in which said spring is provided with a contact member directly engaging said ring.

6. The assembly of claim 1 in which an area of the outer surface of said ring extending substantially semi-circumferentially of said ring provides a zone for finger contact for shifting said ring from latching position into unlatching position.

7. The assembly of claims 1 or 6 in which said ring has a length within the range of approximately 30% to 150% of its outside diameter.

8. The assembly of claim 1 in which said arcuate projection has an angular dimension within the range of about 60° to 100°.

9. A dental handpiece assembly comprising a motor section and a handpiece section having a motor casing and a handpiece casing, respectively; each of said sections having a power-transmitting shaft axially disposed therein; said sections normally being arranged in longitudinal alignment with the respectively power-transmitting shafts thereof in operative engagement with each other; and latching means releasably connecting said sections in operative relationship; wherein the improvement comprises said latching means including a tubular latching ring provided by said motor section adjacent said handpiece section; said latching ring having a circumferentially-exposed annular outer surface continuing axially beyond the outer surface of said motor section; means mounting said ring for transverse bidirectional movement between a latching position wherein said ring is coaxial with said motor section and has its outer surface substantially flush with said motor casing and an unlatching position wherein said ring is displaced laterally relative to said motor section; a spring urging said ring into said latching position; said handpiece casing having a tubular neck provided with an annular flange disposed within said ring when said sections are latched together; an arcuate projection provided within said ring and engaging said neck and flange to prevent axial separation of said sections when said ring is in its latching position; said projection being shifted laterally away from said neck and flange when said ring is urged into its unlatching position for axial disconnection of said sections; said spring exerting an outward force upon said ring along a transverse line extending diametrically through said ring; said arcuate projection extending through said transverse line on a side of said ring opposite from said spring; and guide means provided by said ring and motor section for guiding bi-directional movement of said ring along said transverse line between its unlatching and latching positions.

10. The assembly of claim 9 in which said guide means includes a pair of parallel guide surfaces provided by said motor section within said ring; said guide surfaces being parallel with and disposed on opposite sides of said transverse line of movement.

11. The assembly of claim 10 in which said guide means also includes a pair of shoulders provided by said ring; said shoulders having surfaces slidably engaging said guide surfaces of said motor section.

12. The assembly of claim 9 in which said spring is a compression spring equipped with a contact member engaging said ring for urging said ring into its latching position.

13. The assembly of claim 9 in which a semi-circumferential area of the outer surface of said ring bisected by said transverse line of movement provides the finger contact area for shifting said ring from its latching position into its unlatching position.

14. The assembly of claims 9 or 13 in which said ring has a length within the range of about 30% to 150% of the outside diameter thereof.

15. The assembly of claim 9 in which said arcuate projection has an angular dimension within the range of about 60° to 100°.

16. A motor section for a dental handpiece assembly, said motor section having a casing equipped with a pilot sleeve and a motor shaft therein; said motor section also having a latch ring extending about said pilot sleeve and adapted to releasably engage the flange-providing neck portion of a handpiece section; said latch ring having a circumferentially-exposed annular outer surface continuing axially beyond the outer surface of said motor section; means mounting said ring for transverse movement between a latching position wherein said ring is coaxial with said motor section and has its outer surface substantially flush with said casing and an unlatching position wherein said ring is disposed laterally from said motor section; a spring urging said ring into its latching position; and an arcuate projection provided within said ring and adapted to engage the neck and flange of a handpiece section to prevent axial separation of said sections when said ring is in its latching position; said projection being shifted laterally out of engagement with the neck and flange of a handpiece section when said ring is urged into unlatching position.

17. The motor section of claim 16 in which said spring exerts an outward force upon said ring extending along a transverse line of ring movement; said arcuate projection extending through said transverse line of movement.

18. The motor section of claim 17 in which said transverse line of ring movement is fixed relative to said motor section.

19. The motor section of claims 17 or 18 in which said spring is a compression spring disposed along said transverse line of movement on one side of said pilot sleeve, and said arcuate projection is disposed along said transverse line of movement on the opposite side of said pilot sleeve.

20. The motor section of claim 16 in which said ring has a length within the range of about 30% to 150% of the outer diameter thereof; the outer surface of said ring having a finger contact area for the application of force for shifting said ring into its unlatching position having an axial dimension extending the full length of said ring.

21. The motor section of claim 20 in which said contact area also extends semi-circumferentially of said ring, the semi-circumferential dimension of said area being bisected by said transverse line of movement.

22. The motor section of claim 16 in which said arcuate projection has an angular dimension within the range of about 60° to 100°.

* * * * *